United States Patent [19]

Krapcho et al.

[11] 4,004,007
[45] Jan. 18, 1977

[54] 2-HETEROCYCLICALKYL-3,3a,4,5,6,7-HEXAHYDRO-3-PHENYL-7-(PHENYLMETHYLENE)-2H-INDAZOLES

[75] Inventors: John Krapcho, Somerset; Chester Frank Turk, Kendall Park, both of N.J.

[73] Assignee: E. R. Squibb & Sons, Inc., Princeton, N.J.

[22] Filed: Aug. 8, 1975

[21] Appl. No.: 603,222

[52] U.S. Cl. ............................. 424/246; 424/248.4; 424/267; 424/273; 260/243 B; 260/247.5 EP; 260/293.55; 260/310 C; 260/239 BE; 260/240 F; 424/248.58

[51] Int. Cl.² ............. C07D 487/02; A61K 31/395

[58] Field of Search ....... 260/310 C, 240 E, 240 G; 424/248, 267, 273, 246

[56] References Cited

UNITED STATES PATENTS 3,852,279   12/1974   Krapcho et al. ............... 260/240 F
3,897,420   7/1975   Krapcho et al. ............ 260/240 R X

FOREIGN PATENTS OR APPLICATIONS 4,742,267   10/1972   Japan ........................ 260/250 AC Primary Examiner—Allen B. Curtis
Attorney, Agent, or Firm—Lawrence S. Levinson; Merle J. Smith; Burton Rodney

[57] ABSTRACT

Compounds of the formula

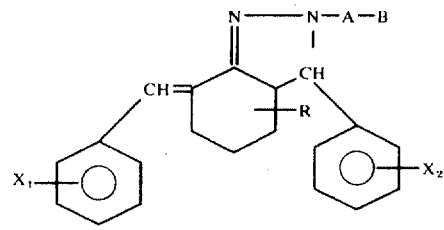

wherein R, $X_1$, $X_2$, A and B are as defined herein, and their N-oxides and acid addition salts thereof, are provided which have been found to possess anti-inflammatory activity. In addition, methods for preparing such compounds, pharmaceutical compositions containing such compounds, and methods for using such compositions as anti-inflammatory agents are also provided.

15 Claims, No Drawings

2-HETEROCYCLICALKYL-3,3a,4,5,6,7-HEXAHYDRO-3-PHENYL-7-(PHENYLMETHYLENE)-2H-INDAZOLES

SUMMARY OF THE INVENTION

The present invention is directed to compounds of the formula

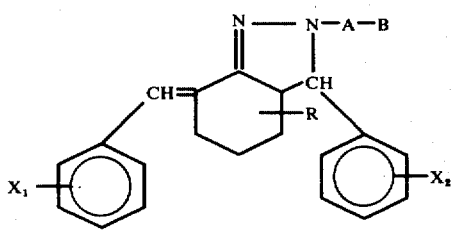

and N-oxides and acid addition salts thereof, wherein $X_1$ and $X_2$ can be the same or different and are hydrogen, F, Cl, lower alkyl, lower alkoxy, or $CF_3$; R is H or lower alkyl, A is straight or branched chain alkylene of 2 to 8 carbons, and B is a 5-, 6- or 7-membered heterocyclic ring which includes a nitrogen atom, and may include the other hetero atom such as sulfur, nitrogen or oxygen. The foregoing compounds possess anti-inflammatory activity.

In addition, this invention encompasses the methods for preparing said compounds, pharmaceutical compositions containing said compounds and methods for using said compositions as anti-inflammatory agents.

The term "lower alkyl" is intended to mean a straight or branched hydrocarbon fragment of from one to six carbon atoms.

The term "lower alkoxy" is intended to mean "lower alkyl-O-".

As indicated, B is a 5-, 6- or 7-membered heterocyclic ring, which includes nitrogen and may include one other hetero atom such as nitrogen, oxygen or sulfur. Examples of such heterocyclic rings include, but are not limited to, piperidino, homopiperidino, pyrrolidino, morpholino, thiamorpholino, piperazino, N-lower alkyl substituted piperazino or N-hydroxyloweralkyl-piperazino.

The "alkylene" group represented by A includes straight or branched chain radicals of 2 to 8 carbons, such as $-(CH_2)_2-$, $-(CH_2)_4-$,

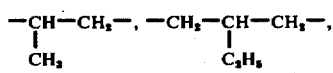

and the like.

Preferred are those compounds of formula I wherein $X_1$ and $X_2$ are the same, A contains 2 to 4 carbons, R is hydrogen, and B is a 6-membered heterocyclic ring. More preferred are those compounds wherein $X_1$ is hydrogen, $X_2$ is hydrogen, R is hydrogen, A contains 2 or 3 carbons, and B is piperidino, piperazinyl, N-alkylpiperazinyl or morpholinyl.

The term "acid-addition salts" is intended to mean salts which may be formed for the purpose of isolation, purification and storage, such as the oxalate salt, etc. and pharmaceutically acceptable salts meant for administration of the compound to a host, such as the hydrochloride, sulfate, acetate, citrate, etc.

The new compounds of formula I are prepared by reacting the appropriate cycloalkylone represented by formula

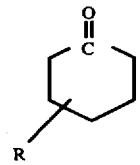

with a substituted benzaldehyde of the formula

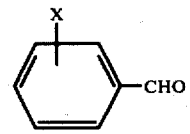

to produce the intermediate of the formula

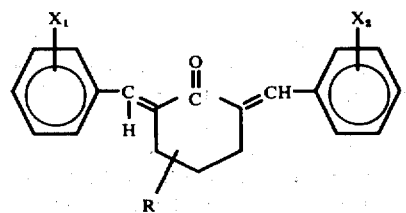

The compounds of formula IV are converted to a compound of formula I by reaction with a hydrazine of the formula

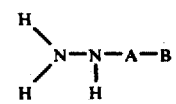

in an organic solvent, preferably an alcohol of up to four carbon atoms at temperatures of from about 40° to about 120° C, preferably at about the reflux temperature of the solvent, for from about ½ hour to about 12 hours, preferably for about 4 hours.

The hydrazine of formula V is prepared by reacting a heteroalkylene halide, B-A-halo, with an excess of hydrazine $H_2NNH_2$.

Alternatively, compounds of formula IV can be reacted with a hydroxyalkyl hydrazine of the formula

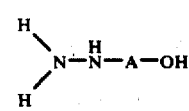

to form the alcohol of the formula

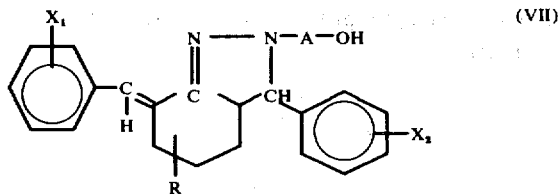

The alcohol of formula VII is reacted by heating with p-toluenesulfonyl chloride to form the tosylate of formula

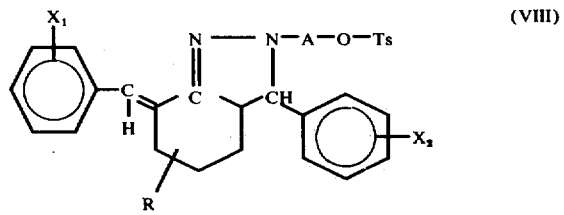

which in turn is treated with the heterocyclic compound of formula HB to form the compounds of formula I.

All of the starting materials in the above reactions as well as the reaction conditions and techniques are conventional in nature as will be apparent to one skilled in the art.

A compound of formula I may be converted to its N-oxide by reaction with an oxidizing agent such as hydrogen peroxide, peracetic acid and so forth.

The compounds of the present invention, their N-oxides, and their non-toxic pharmaceutically acceptable mono- or di-acid addition salts are useful as anti-inflammatory agents in mammalian species, e.g., rats and mice, as indicated by the passive cutaneous anaphylaxis test in the rat [Ref: Ovary, Z and Bier, O.G., Proc. Soc. Exp. Biol. Med. 81:584, 1952 and Goose, J. and Blair, A. M. J. N., Immunology, 16:749, 1969], when administered in amounts ranging from about 0.5 mg/kg to about 10.0 mg/kg of body weight per day. A preferred dosage regimen for optimum results is from about 1 mg to about 5 mg per kg of body weight per day, and such dosage units are employed that a total of about 35 mg to about 7 g of active ingredient are administered in a 24-hour period for a subject of about 70 kg body weight.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard of soft gelatin, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples illustrate the present invention, without, however, limiting the same thereto. All temperatures are expressed in degrees Centigrade.

EXAMPLE 1

3,3a,4,5,6,7-Hexahydro-3-Phenyl-7-(Phenylmethylene)-2-[3-(1-piperidinyl)propyl]-2H-indazole, maleate salt (1:1)

A. 2,6-Bis(phenylmethylene)cyclohexanone

A solution of 32.0 g (0.33 mole) of cyclohexanone, 70.0 g (0.66 mole) of benzaldehyde, 200 ml of ethanol and 20 ml of concentrated HCl is heated and then refluxed for one hour. Crystallization from the deep red solution occurs and after cooling the crystallized 2,6-bis(phenylmethylene)cyclohexanone is filtered and washed with cold ethanol and dried yielding 72.0 g; m.p. 114°–116°. This material is recrystallized from 120 ml of DMF (dimethylformamide) yielding 56.0 g (63%) of yellow 2,6-bis(phenylmethylene)cyclohexanone; m.p. 114°–116°.

B. N-(3-Hydrazinopropyl)piperidine

Forty grams (0.20 mole) of N-(3-chloropropyl)-piperidine · HCl and 30 ml of anhydrous $N_2H_4$ are reacted in 160 ml of ethanol by the method of Nagrody and Morris, Can. J. Chem., 47, 2001 (1969). The halide in ethanol is added as a warm solution because of its limited solubility in cold ethanol. The yield of the desired hydrazine is 13.6 g (43%); b.p. 135°–138°/18 mm. Lit. b.p. 133°–135°/20 mm.

C. 3,3a,4,5,6,7-Hexahydro-3-phenyl-7-(phenylmethylene)-2-[3-(1-piperidinyl)propyl]-2H-indazole, maleate salt A stirred mixture of 2,6-bis(phenylmethylene)cyclohexanone (8.8 g; 0.032 mole), 5.1 g (0.032 mole) of the above hydrazine and 80 ml of methanol is heated and the resulting solution refluxed for 4 hours. The bulk of the solvent is removed on a rotary evaporator and the viscous residue (14.1 g) is dissolved in 250 ml of ether and then extracted with 50 ml portions of water (six times). The ether phase is dried over $MgSO_4$, filtered and the solvent evaporated to give 13.0 g of viscous base. A warm solution of the latter in 50 ml of MeCN is treated with a warm solution of 2.8 g of oxalic acid in 30 ml of MeCN. On rubbing, the crystalline oxalate salt separates; wt., after cooling overnight, 13.0 g; m.p. 178°–180° (foaming); s. 170°. Following crystallization from 25 ml of hot DMF - 80 ml MeCN, the cream-colored solid weighs 11.6 g; m.p. 172°–174° (foaming).

The oxalate salt is converted to the base ($K_2CO_3$; ether extractions) and the latter (9.3 g) and 2.6 g of maleic acid are dissolved in 60 ml of warm MeCN and diluted to 600 ml with ether. After prolonged rubbing and subsequent cooling, the crystalline maleate salt slowly separates; crude yield, 8.5 g (50%); m.p. 121°–122° (s. 117°). Crystallization from 60 ml methanol - 700 ml ether gives 7.7 g (45%) of nearly colorless product; m.p. 146°–148°.

EXAMPLE 2

3,3a,4,5,6,7-Hexahydro-2-[3-(4-methyl-1-piperazinyl)-propyl]-3-phenyl-7-(phenylmethylene)-2H-indazole, maleate salt (1:2)

A. 1-(3-Hydrazinopropy)-4-methylpiperazine

Nineteen grams (0.05 mole) of 1-(3-bromopropyl)-4-methylpiperazine.2HBr [prepared as described in Krapcho and Turk, J. Med. Chem., 9, 191, (1966)] is pulverized and added to a stirred solution of 16 ml (0.5 mole) of anhydrous $N_2H_4$ in 50 ml of ethanol. The temperature rises gradually to 48° before subsiding. The mixture is then refluxed for 4 hours and kept overnight at room temperature.

The heavy lower layer is separated, extracted with ethanol, and the combined ethanol layers are concentrated in a rotary evaporator. The oily residue (11.0 g) is distilled to give 5.8 g (68%) of a colorless oil; b.p. 100°–103°/1 mm. The material is hygroscopic and picks up $CO_2$ readily.

B. 3,3a,4,5,6,7-Hexahydro-2-[3-(4-methyl-1-piperazinyl)-propyl]-3-phenyl-7-(phenylmethylene)-2H-indazole maleate salt (1:2)

2,6-Bis(phenylmethylene)cyclohexanone (8.8 g; 0.032 mole) is reacted with the above hydrazine as prepared in part A (5.5 g; 0.032 mole) in 80 ml of methanol as described under Part C of Example 1 to give 16 g of crude oily base. The crude dioxalate salt weighs 16.1 g; m.p. 200°–202°(dec.). Following crystallization from 50 ml hot DMF - 100 ml MeCN, the cream colored solid weighs 13.9 g; m.p. 204°–206°(dec.).

The dioxalate salt is converted to the base ($K_2CO_3$; ether extractions) and the latter (8.3 g) and 4.5 g of maleic acid are dissolved in 140 ml of warm MeCN; the solid dimaleate salt separates. After crystallizing at room temperature the mixture is cooled overnight; wt. 12.1 g (65%); m.p. 179°–181°. Crystallization from 30 ml hot DMF - 80 ml MeCN gives 10.7 g (57%) of cream colored material; m.p. 179°–181°.

EXAMPLE 3

3,3a,4,5,6,7-Hexahydro-2-[3-(4-morpholinyl)-propyl]-3-phenyl-7-(phenylmethylene)-2H-indazole, hydrochloride (1:1)

A. N-(3-Chloropropyl)morpholine, hydrochloride

Trimethylene chlorobromide (180 g; 1.15 moles) and 150 g (1.72 moles) of morpholine are reacted in 450 ml of benzene by the method of Adams and Whitmore, JACS, 67, 736 (1945). However, instead of extracting with HCl as in the reference, the solvents are evaporated and the residue distilled to give 76.8 g of colorless oil; b.p. 112°–117°/25 mm. Lit. b.p., 113°–115°/25 mm. The product is dissolved in 1.2 l. of ether, cooled, stirred, and treated with 58 ml. of 8.2 N alcoholic HCl to precipitate the solid HCl salt; yield, 81.6 g (36%); m.p. 164°–166°.

B. N-(3-Hydrazinopropyl)morpholine

The above material as prepared in part A (40 g; 0.20 mole) and 30 ml of anhydrous $N_2H_4$ are reacted in 160 ml of ethanol by the method of Nagrody and Morris, Can. J. Chem., 47, 2001 (1969). The halide in ethanol is added as a warm solution because of its limited solubility in cold ethanol. A colorless oil is obtained; 17.7 g (56%); b.p. 115°–119°/1 mm.

C. 3,3a,4,5,6,7-Hexahydro-2-[3-(4-morpholinyl)-propyl]-3-phenyl-7-(phenylmethylene)-2H-indazole, hydrochloride 2,6-Bis(phenylmethylene)cyclohexanone (8.8 g; 0.032 mole) and 5.2 g (0.033 mole) of the above hydrazine as prepared in part A are reacted in 80 ml of methanol as described under part C, Example 1, to give 12.8 g of a semi-solid crude base which is crystallized from 60 ml of MeCN to yield 8.2 g of pale yellow solid; m.p. 98°–100°.

A stirred suspension of the base (7.9 g) in 40 ml of MeCN is treated with 2.4 ml of 8.2 N alcoholic HCl and the resulting solution diluted to 300 ml with ether. On rubbing, the crystalline HCl salt gradually separates; crude yield, after cooling overnight, 8.0 g (55%); m.p. 134°–136° (s. 125°). Following crystallization from 40 ml warm methanol-400 ml ether, the nearly colorless product weighs 7.0 g (49%); m.p. 137°–139°.

EXAMPLES 4 to 14

Following the procedure of Example 1 but substituting for benzaldehyde in part A, the compound indicated in column I, there is obtained the corresponding compound of formula I (corresponding to Example 1) wherein each X (that is $X_1$ and $X_2$), and its position, is as indicated in column II:

| Example | I | II |
|---|---|---|
| 4 | o-chlorobenzaldehyde | 2-chloro |
| 5 | p-chlorobenzaldehyde | 4-chloro |
| 6 | p-fluorobenzaldehyde | 4-fluoro |
| 7 | 2-methylbenzaldehyde | 2-methyl |
| 8 | 3-methylbenzaldehyde | 3-methyl |
| 9 | 4-methylbenzaldehyde | 4-methyl |
| 10 | 2-methoxybenzaldehyde | 2-methoxy |
| 11 | 3-methoxybenzaldehyde | 3-methoxy |
| 12 | 4-methoxybenzaldehyde | 4-methoxy |
| 13 | 4-butoxybenzaldehyde | 4-butoxy |
| 14 | 3-trifluoromethylbenzaldehyde | 3-trifluoromethyl |

EXAMPLES 15 to 25

Following the procedure of Example 1 and Example 2 but substituting for benzaldehyde in Example 1 part A, the compound indicated in column I, there is obtained the corresponding compound of formula I (corresponding to the compound formed in Example 2) wherein each X (that is $X_1$ and $X_2$), and its position, is as indicated in column II:

| Example | I | II |
|---|---|---|
| 15 | o-chlorobenzaldehyde | 2-chloro |
| 16 | p-chlorobenzaldehyde | 4-chloro |
| 17 | p-fluorobenzaldehyde | 4-fluoro |
| 18 | 2-ethylbenzaldehyde | 2-ethyl |
| 19 | 3-methylbenzaldehyde | 3-methyl |

-continued

| Example | I | II |
|---|---|---|
| 20 | 4-propylbenzaldehyde | 4-propyl |
| 21 | 2-methoxybenzaldehyde | 2-methoxy |
| 22 | 3-ethoxybenzaldehyde | 3-ethoxy |
| 23 | 4-propoxybenzaldehyde | 4-propoxy |
| 24 | 3-butoxybenzaldehyde | 3-butoxy |
| 25 | 4-trifluoromethylbenzaldehyde | 4-trifluoromethyl |

EXAMPLES 26 to 36

Following the procedure of Example 1 and Example 3 but substituting for benzaldehyde in Example 1 part A, the compound indicated in column I, there is obtained the corresponding compound of formula I (corresponding to the compounds formed in Example 3) wherein each X (that is $X_1$ and $X_2$), and its position, is as indicated in column II:

| Example | I | II |
|---|---|---|
| 26 | o-chlorobenzaldehyde | 2-chloro |
| 27 | p-chlorobenzaldehyde | 4-chloro |
| 28 | p-fluorobenzaldehyde | 4-fluoro |
| 29 | 2-methylbenzaldehyde | 2-methyl |
| 30 | 3-methylbenzaldehyde | 3-methyl |
| 31 | 4-methylbenzaldehyde | 4-methyl |
| 32 | 2-methoxybenzaldehyde | 2-methoxy |
| 33 | 3-methoxybenzaldehyde | 3-methoxy |
| 34 | 4-methoxybenzaldehyde | 4-methoxy |
| 35 | 4-butoxybenzaldehyde | 4-butoxy |
| 36 | 3-trifluoromethylbenzaldehyde | 3-trifluoromethyl |

EXAMPLES 37 - 57

Following the procedure of Example 1 but substituting for N-(3-chloropropyl)piperidine in part B, the compound indicated in column I, there is obtained the corresponding compound of formula I (corresponding to Example 1) wherein -A-B is the group indicated in column II:

| Ex. No. | I | II |
|---|---|---|
| 37 | Cl(CH₂)₂—N(piperidine) | —(CH₂)₂—N(piperidine) |
| 38 | Br—(CH₂)₄—N(piperidine) | —(CH₂)₄—N(piperidine) |
| 39 | Cl—CH₂CHCH₂—N(piperidine), CH₃ | —CH₂CHCH₂—N(piperidine), CH₃ |
| 40 | Cl—(CH₂)₃—N(piperazine)NH | —(CH₂)₃—N(piperazine)NH |
| 41 | Br—(CH₂)₅—N(piperazine)NH | —(CH₂)₅—N(piperazine)NH |
| 42 | Cl—CH₂CH₂CH₂CHCH₂—N(piperazine)NH, C₂H₅ | —CH₂CH₂CH₂CHCH₂—N(piperazine)NH, C₂H₅ |
| 43 | Cl—(CH₂)₄—N(morpholine)O | —(CH₂)₄—N(morpholine)O |
| 44 | Cl—(CH₂)₆—N(morpholine)O | —(CH₂)₆—N(morpholine)O |
| 45 | Cl—(CH₂)₇—N(morpholine)O | —(CH₂)₇—N(morpholine)O |
| 46 | Cl—(CH₂)₂—N(thiomorpholine)S | —(CH₂)₂—N(thiomorpholine)S |

| Ex. No. | I | II |
|---|---|---|
| 47 | Cl—(CH₂)₃—N⟨cycloheptyl⟩ | —(CH₂)₃—N⟨cycloheptyl⟩ |
| 48 | Cl—(CH₂)₅—N⟨cyclooctyl⟩ | —(CH₂)₅—N⟨cyclooctyl⟩ |
| 49 | Cl—(CH₂)₃—N⟨aziridine⟩ | —(CH₂)₃—N⟨aziridine⟩ |
| 50 | Br—(CH₂)₈—N⟨aziridine⟩ | —(CH₂)₈—N⟨aziridine⟩ |
| 51 | Cl—CH₂CHCH₂—N⟨aziridine⟩, C₂H₅ | —CH₂—CHCH₂—N⟨aziridine⟩, C₂H₅ |
| 52 | Cl—(CH₂)₄—N⟨piperazine⟩N—C₂H₅ | —(CH₂)₄—N⟨piperazine⟩N—C₂H₅ |
| 53 | Cl—CH₂CH₂CHCH₂—N⟨piperazine⟩N—C₄H₉, CH₃ | —CH₂CH₂CHCH₂—N⟨piperazine⟩N—C₄H₉, CH₃ |
| 54 | Br—(CH₂)₂—N⟨piperazine⟩N—C₂H₅ | —(CH₂)₂—N⟨piperazine⟩N—C₂H₅ |
| 55 | Cl—(CH₂)₃—N⟨piperazine⟩N—CH₂CH₂OH | —(CH₂)₃—N⟨piperazine⟩N—CH₂CH₂OH |
| 56 | Cl—CH₂CHCH₂—N⟨piperazine⟩N—(CH₂)₂OH, C₂H₅ | —CH₂CHCH₂—N⟨piperazine⟩N—(CH₂)₂OH, C₂H₅ |
| 57 | Cl—(CH₂)₆—N⟨piperazine⟩N—CH₂CH₂OH | —(CH₂)₆—N⟨piperazine⟩N—CH₂CH₂OH |

EXAMPLES 58 to 63

Following the procedure of Example 1A, upon substituting in place of the cyclohexanone, one of the following:

4-methylcyclohexanone
4-ethylcyclohexanone
4-n-propylcyclohexanone
4-t-butylcyclohexanone
3-methylcyclohexanone
3-ethylcyclohexanone one obtains the following:

2,6-bis(phenylmethylene)(4-methylcyclohexanone)
2,6-bis(phenylmethylene)(4-ethylcyclohexanone)
2,6-bis(phenylmethylene)(4-n-propylcyclohexanone)
2,6-bis(phenylmethylene)(4-t-butylcyclohexanone)
2,6-bis(phenylmethylene)(3-methylcyclohexanone)
2,6-bis(phenylmethylene)(3-ethylcyclohexanone)

Upon substituting the above compound in Example 1 in place of the 2,6-bis(phenylmethylene)cyclohexanone, one obtains the following:

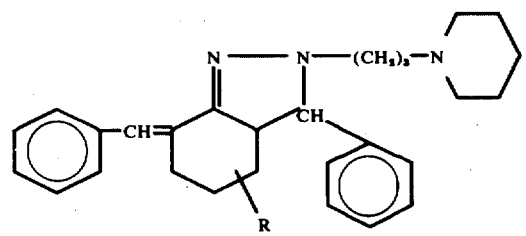

| | R |
|---|---|
| 58. | 5-methyl |
| 59. | 5-ethyl |

-continued

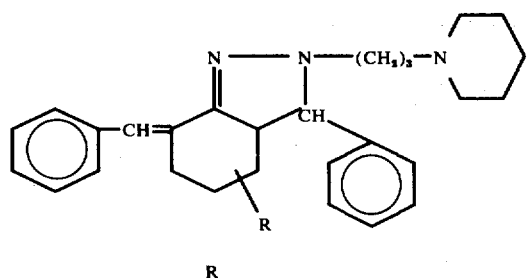

| | R |
|---|---|
| 60. | 5-n-propyl |
| 61. | 5-t-butyl |
| 62. | 4 and/or 6-methyl |
| 63. | 4 and/or 6-ethyl |

EXAMPLES 64 to 69

Following the procedure of Example 1A, upon substituting in place of the cyclohexanone, one of the following:
4-methylcyclohexanone
4-ethylcyclohexanone
4-n-propylcyclohexanone
4-t-butylcyclohexanone
3-methylcyclohexanone
3-ethylcyclohexanone
one obtains the following:
2,6-bis(phenylmethylene)(4-methylcyclohexanone)
2,6-bis(phenylmethylene)(4-ethylcyclohexanone
2,6-bis(phenylmethylene)(4-n-propylcyclohexanone)
2,6-bis(phenylmethylene)(4-t-butylcyclohexanone)
2,6-bis(phenylmethylene)(3-methylcyclohexanone)
2,6-bis(phenylmethylene)(3-ethylcyclohexanone)

Upon substituting the above compounds in Example 2C in place of the 2,6-bis(phenylmethylene)cyclohexanone, one obtains the following:

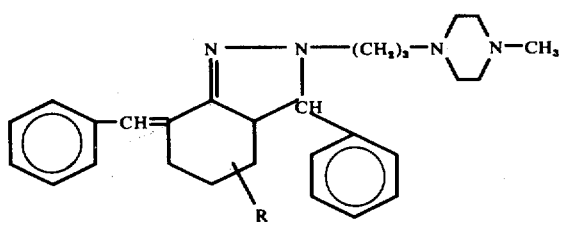

| | R |
|---|---|
| 64. | 5-methyl |
| 65. | 5-ethyl |
| 66. | 5-n-propyl |
| 67. | 5-t-butyl |
| 68. | 4 and/or 6-methyl |
| 69. | 4 and/or 6-ethyl |

EXAMPLES 70 to 75

Following the procedure of Example 1A, upon substituting in place of the cyclohexanone, one of the following:
4-methylcyclohexanone
4-ethylcyclohexanone
4-n-propylcyclohexanone
4-n-butylcyclohexanone
3-methylcyclohexanone
3-ethylcyclohexanone
one obtains the following:
2,6-bis(phenylmethylene)(4-methylcyclohexanone)
2,6-bis(phenylmethylene)(4-ethylcyclohexanone)
2,6-bis(phenylmethylene)(4-n-propylcyclohexanone)
2,6-bis(phenylmethylene)(4-n-butylcyclohexanone)
2,6-bis(phenylmethylene)(3-methylcyclohexanone)
2,6-bis(phenylmethylene)(3-ethylcyclohexanone)

Upon substituting the above compounds in Example 3C in place of the 2,6-bis(phenylmethylene)cyclohexanone, one obtains the following:

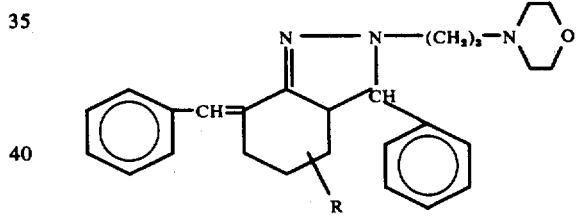

| | R |
|---|---|
| 70. | 5-methyl |
| 71. | 5-ethyl |
| 72. | 5-n-propyl |
| 73. | 5-n-butyl |
| 74. | 4 and/or 6-methyl |
| 75. | 4 and/or 6-ethyl |

EXAMPLES 76–88

Following the procedure of Example 1, but substituting for the benzaldehyde (in part A of Example 1), the compound indicated in column I, substituting for the cyclohexanone, the compound indicated in column II, substituting for the N-(3-chloropropylpiperidine·HCl, the compound listed in column III, there is obtained the corresponding compound of formula I wherein $X_1$, $X_2$, R, A and B are as indicated in column IV:

| | I | II | III | | IV | | | |
|---|---|---|---|---|---|---|---|---|
| Ex. | $X_1$ | R | X—A—B | $X_1$ | $X_2$ | R | A | B |
| 76 | o-F | H | Cl—(CH$_2$)$_3$—N⟨piperazine⟩NH | o-F | same as $X_1$ | H | (CH$_2$)$_3$ | —N⟨piperazine⟩NH |
| 77 | p-Cl | 4-C$_2$H$_5$ | Cl—(CH$_2$)$_4$—N⟨pyrrolidine⟩ | p-Cl | " | 5-C$_2$H$_5$ | (CH$_2$)$_4$ | —N⟨pyrrolidine⟩ |
| 78 | 3-C$_2$H$_5$ | 4-C$_3$H$_7$ | Cl—(CH$_2$)$_2$—N⟨morpholine⟩O | 3-C$_2$H$_5$ | " | 5-C$_3$H$_7$ | (CH$_2$)$_2$ | —N⟨morpholine⟩O |
| 79 | 4-CH$_3$O | 4-C$_4$H$_9$ | Cl—CH$_2$—N⟨piperazine⟩N—CH$_2$CH$_2$OH | 4-CH$_3$O | " | 5-C$_4$H$_9$ | CH$_2$ | —N⟨piperazine⟩NCH$_2$CH$_2$OH |
| 80 | 4-CF$_3$ | 3-CH$_3$ | Cl—(CH$_2$)$_3$—N⟨piperidine⟩ | 4-CF$_3$ | " | 4- and/or 6-CH$_3$ | (CH$_2$)$_3$ | —N⟨piperidine⟩ |
| 81 | 3-C$_4$H$_9$O | 3-CH$_3$ | Cl—(CH$_2$)$_3$—N⟨piperazine⟩NH | 3-C$_4$H$_9$O | " | 4- and/or 6-CH$_3$ | (CH$_2$)$_3$ | —N⟨piperazine⟩NH |
| 82 | H | 3-C$_5$H$_5$ | Cl—(CH$_2$)$_4$—N⟨piperazine⟩N—C$_2$H$_5$ | H | " | 4- and/or 6-C$_5$H$_5$ | (CH$_2$)$_4$ | —N⟨piperazine⟩N—C$_2$H$_5$ |
| 83 | 3-C$_3$H$_7$O | 4-C$_3$H$_7$ | Cl—(CH$_2$)$_2$—N⟨morpholine⟩O | 3-C$_3$H$_7$O | " | 5-C$_3$H$_7$ | (CH$_2$)$_2$ | —N⟨morpholine⟩O |
| 84 | 2-C$_3$H$_5$ | H | Cl—(CH$_2$)$_3$—N⟨pyrrolidine⟩ | 2-C$_3$H$_5$ | " | H | (CH$_2$)$_3$ | —N⟨pyrrolidine⟩ |
| 85 | 3-C$_3$H$_5$O | 4-C$_4$H$_9$ | Cl—(CH$_2$)$_2$—N⟨thiomorpholine⟩S | 3-C$_3$H$_5$O | " | 5-C$_4$H$_9$ | (CH$_2$)$_2$ | —N⟨thiomorpholine⟩S |
| 86 | 4-C$_5$H$_{11}$ | H | Cl—(CH$_2$)$_3$—N⟨azocane⟩ | 4-C$_5$H$_{11}$ | " | H | (CH$_2$)$_3$ | —N⟨azocane⟩ |
| 87 | 4-C$_6$H$_{13}$O | 3-C$_5$H$_{11}$ | Cl—(CH$_2$)$_4$—N⟨pyrrolidine⟩ | 4-C$_6$H$_{13}$O | " | 4- and/or 6-C$_5$H$_{11}$ | (CH$_2$)$_4$ | —N |
| 88 | o-Cl | 4-C$_6$H$_{13}$ | Cl—(CH$_2$)$_2$—N⟨thiomorpholine⟩S | o-Cl | " | 5-C$_6$H$_{13}$ | (CH$_2$)$_2$ | —N⟨thiomorpholine⟩S |

EXAMPLE 89

Preparation of capsule formulation

| Ingredient | Milligrams per Capsule |
|---|---|
| 3,3a,4,6,7-hexahydro-3-phenyl-7-(phenylmethylene)-2-[3-(1-piperidinyl)-propyl]-2H-indazole, maleate salt (1:1) | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 90

Preparation of tablet formation

| Ingredient | Milligrams per Tablet |
|---|---|
| 3,3a,4,6,7-hexahydro-2-[3-(4-methyl-1-piperazinyl)propyl]-3-phenyl-7-(phenylmethylene)-2H-indazole, maleate salt (1:2) | 300 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 300 milligrams of active ingredient.

EXAMPLE 91

Preparation of oral syrup formulation

| Ingredient | Amount |
|---|---|
| 3,3a,4,5,6,7-hexahydro-2-[3-(4-morpholinyl)-propyl]-3-phenyl-7-(phenylmethylene)-2H-indazole, hydrochloride (1:1) | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.C. & C. No. 2) | 10 mg. |
| Cherry flavor | 50 mg. |
| Distilled water qs to | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A compound of the formula

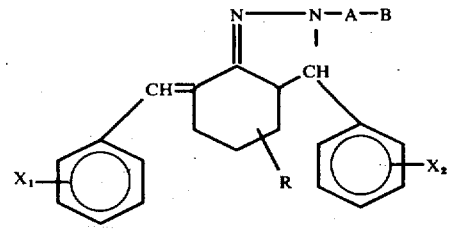

wherein $X_1$ and $X_2$ are the same or different and are selected from the group consisting of hydrogen, F, Cl, lower alkyl, lower alkoxy, or $CF_3$; R is selected from the group consisting of hydrogen or lower alkyl, A is a straight or branched chain alkylene group of from 2 to about 8 carbons, and B is a 5-, 6-, or 7-membered heterocyclic ring selected from the group consisting of piperidinyl, homopiperidinyl, pyrrolidinyl, morpholinyl, thiamorpholinyl, piperazinyl, N-lower alkylpiperazinyl and N-hydroxy-lower alkylpiperazinyl; and N-oxides and pharmaceutically acceptable acid addition salts thereof.

2. A compound as defined in claim 1 wherein $X_1$ and $X_2$ are the same.
3. A compound as defined in claim 1 wherein $X_1$ and $X_2$ are hydrogen.
4. A compound as defined in claim 1 wherein one of $X_1$ and $X_2$ is hydrogen.
5. A compound as defined in claim 1 wherein $X_1$ and $X_2$ are the same or different and are selected from the group consisting of hydrogen, lower alkyl, F or Cl.
6. A compound as defined in claim 1 wherein $X_1$ and $X_2$ are the same or different and are selected from the group consisting of hydrogen, lower alkoxy or $CF_3$.
7. A compound as defined in claim 1 wherein R is hydrogen.
8. A compound as defined in claim 1 wherein R is lower alkyl.
9. A compound as defined in claim 1 wherein A contains 2 to 4 carbons.
10. A compound as defined in claim 1 wherein B is morpholinyl, piperazinyl or piperidinyl.
11. A compound of claim 1 having the name 3,3a,4,6,7-hexahydro-3-phenyl-7-(phenylmethylene)-2-[3-(1-piperidinyl)propyl]-2H-indazole or its maleate salt.
12. A compound as defined in claim 1 having the name 3,3a,4,6,7-hexahydro-2-[3-(4-methylpiperazinyl)-propyl]-3-phenyl-7-(phenylmethylene)-2H-indazole or its maleate salt.
13. A compound as defined in claim 1 having the name 3,3a,4,5,6,7-hexahydro-2-[3-(4-morpholinyl)-propyl]-3-phenyl-7-(phenylmethylene)-2H-indazole or its hydrochloride salt.
14. An anti-inflamatory composition comprising an effective amount of the compound of claim 1 in combination with a pharmaceutically acceptable carrier.
15. A method of treating inflammation in mammalian species, which comprises administering to a mammalian host a therapeutic amount of a compound as defined in claim 1.

* * * * *